United States Patent [19]

Whalley et al.

[11] Patent Number: 5,037,779
[45] Date of Patent: Aug. 6, 1991

[54] METHOD OF ENCAPSULATING A SENSOR DEVICE USING CAPILLARY ACTION AND THE DEVICE SO ENCAPSULATED

[76] Inventors: Peter D. Whalley, 23, Fairfields, Great Kingshill, Buckinghamshire, HP15 6EP; Stephen D. Evans, 181, Ashford Avenue, Hayes, Middlesex, UB4 OND; John E. A. Shaw, 45, Colne Avenue, West Drayton, Middlesex, UB7 7AL, all of England

[21] Appl. No.: 524,005

[22] Filed: May 16, 1990

[30] Foreign Application Priority Data

May 19, 1989 [GB] United Kingdom ................ 8911607

[51] Int. Cl.$^5$ .................. H01L 21/56; H01L 21/60
[52] U.S. Cl. .................. 437/211; 437/219; 437/901; 357/72
[58] Field of Search .......... 437/211, 219, 901, 927, 437/214, 207; 357/72

[56] References Cited

U.S. PATENT DOCUMENTS 4,697,203 9/1987 Sakai et al. ................ 357/72

FOREIGN PATENT DOCUMENTS

| 0193251 | 9/1986 | European Pat. Off. |
|---|---|---|
| 55-82455 | 6/1980 | Japan .................. 357/72 |
| 58-21358 | 2/1983 | Japan .................. 357/72 |
| 59-84448 | 5/1984 | Japan .................. 437/211 |
| 61-32535 | 2/1986 | Japan .................. 437/211 |
| 61-271859 | 12/1986 | Japan .................. 357/72 |
| 63-197361 | 10/1988 | Japan .................. 437/214 |

OTHER PUBLICATIONS

European Patent Application No. 883061863 (Pub. No. 0300641), Alastair Sibbald et al., 7-7-88.

Primary Examiner—Olik Chaudhuri
Assistant Examiner—David E. Graybill
Attorney, Agent, or Firm—Fleit, Jacobson, Cohn, Price, Holman & Stern

[57] ABSTRACT

A capillary fill encapsulation technique and a device so encapsulated is described such that a selected region of a device may be encapsulated while leaving other regions of the device uncovered.

9 Claims, 3 Drawing Sheets

METHOD OF ENCAPSULATING A SENSOR DEVICE USING CAPILLARY ACTION AND THE DEVICE SO ENCAPSULATED

The present invention relates to a method of encapsulating devices and has particular, though not exclusive, relevance to electronic devices.

A difficulty exists in reliably and accurately encapsulating devices in a manner which lends itself to high volume production, especially where one or more areas of the device must be left uncovered by the encapsulant material. This is the case, for example, where the device in question includes an ion-selective field effect transistor (ISFET) of the king having its gate region treated to render it selective of a chosen constituent of a fluid under test. In these circumstances, the gate region of the ISFET must remain capable of exposure to the field in question whilst other regions of the device need to be encapsulated.

Although the devices in question are typically electronic semi-conductive devices, the invention is also applicable to microelectronic devices such as microengineered structures and small screen printed devices, and small-scale optical devices such as optical-fibre connectors.

An object of this invention is to provide a method whereby a selected region of a device may be reliably and accurately encapsulated whilst leaving at least one other region of the device uncovered by the encapsulant material, and another object is to provide devices that are so selectively encapsulated.

According to the invention there is provided a method of applying a liquid encapsulant to a first region of a device but not to a second region of said device, the method comprising the steps of:

(a) defining a passageway along which said encapsulant can be drawn by capillary action, said passageway being bounded in part by said first region of said device, along which said encapsulant can be drawn by capillary action, and in part by a cover member overlying said device and formed with an aperture, substantially registering with said second region, of dimensions sufficient to inhibit said capillary action at said second region, (b) introducing said encapsulant into said passageway so as to cover said first region whilst leaving said second region uncovered due to said inhibition of said capillary action, and (c) allowing or causing said encapsulant to cure to render said encapsulant material substantially immobile in relation to said device.

The invention also encompasses devices encapsulated in accordance with the foregoing method.

In order that the invention may be clearly understood and readily carried into effect, some embodiments thereof will now be described, by way of example only, with reference to the accompanying drawings of which:

Figure 1:
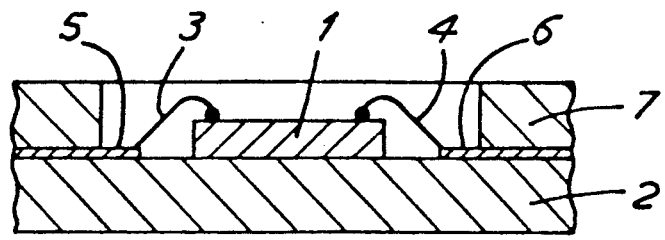
FIG. 1 shows, in cross-sectional view, a semiconductor device and some associated components prior to encapsulation by a method in accordance with one example of the invention.
Figure 2:
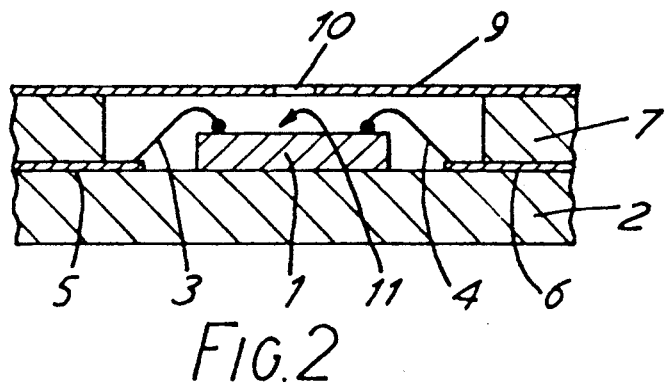
FIG. 2 shows, in view similar to FIG. 1, a subsequent step in the method.
Figure 4:
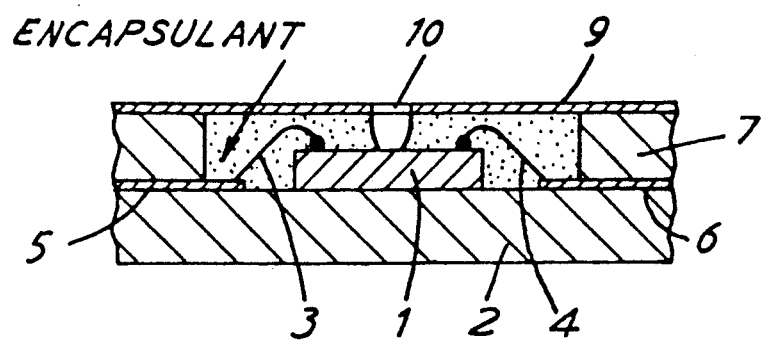

FIG. 4 shows, in similar view to FIGS. 1 and 2, the encapsulating stage of the method; and FIGS. 5, 6, 7, 8 and 9 show, in similar views to FIGS. 1, 2 and 4, alternative methods in accordance with other examples of the invention.

European Patent Application No. 883061863 (publication No. 0300641) describes a process by which two components can be joined together by the use of a porous gasket, to which is added a liquid adhesive. Capillary action ensures a complete and uniform distribution of the adhesive throughout the porous gasket, guaranteeing a firm bond of defined geometry after the adhesive dries. The present invention describes a process whereby a low-to-moderate viscosity encapsulant is drawn into a narrow space by capillary action to cover and protect metallic interconnects whilst leaving the chemically sensitive regions of the chip uncontaminated and able subsequently to be exposed to solution.

FIG. 1 shows an ISFET 1 mounted on a substrate 2 and wire bonded as at 3, 4 in a conventional manner to conductive tracks 5, 6 formed on the substrate 2 in a known manner. A spacer 7 of a thickness slightly greater than the ISFET chip surrounds the chip except for a small opening 8, FIG. 3, which is left to allow the later introduction of the encapsulant. A sheet 9 of transparent material (conveniently a thin sheet of polyester about 30 m) with a hole 10 through the sheet 9 of lateral dimension slightly larger than that of the sensitive region 11 on the chip 1 is located with the hole 10 over the chemically sensitive region 11 of the chip 1. An arrangement as shown in FIG. 2 is then obtained. A plan view is represented in FIG. 3.

Figure 5:
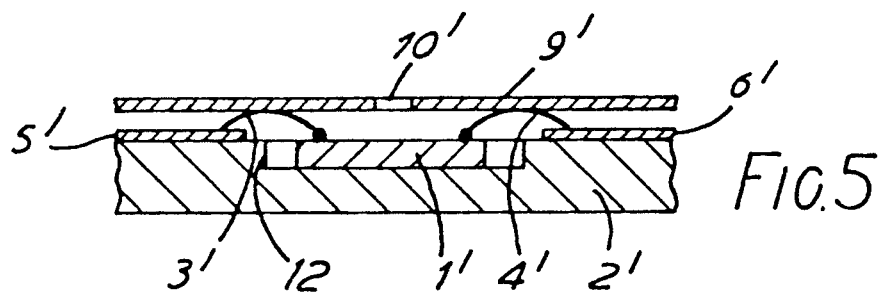
Figure 6:
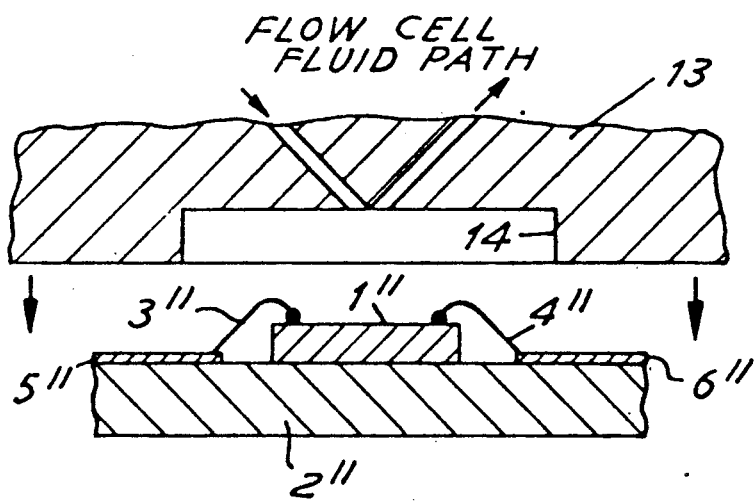

The spacer 7 by holding the sheet 10 to 200 m above the chip 1, prevents the bond wires 3, 4 from being pressed down sufficiently to contact the edge of the chip 1 as this may result in a short-circuit. This can be achieved by locating the chip 1 in a depression or hole 12 in a solid substrate 2' (e.g. alumina) or in flexible substrates (polyimide sheet) as indicated by FIG. 5. The bond wire 3 or 4 and the ball formed in the wire bonding process may contact and support the thin sheet material 9 as long as distortion of the wires 3, 4 does not lead to contact faults. A further possibility is shown in FIG. 6, whereby the chip 1 is mounted as before on a planar substrate 2 and is surmounted by a flow cell cap 13 (used to introduce the solution under test to the chemically sensitive gate region of the ISFET) which incorporates a spacer component 14 to prevent bond wire 3, 4 damage and an opening (not shown) to allow the encapsulant to be introduced. Such a flow cell cap 13 can be readily mass produced by a technique such as injection moulding.

Figure 3:
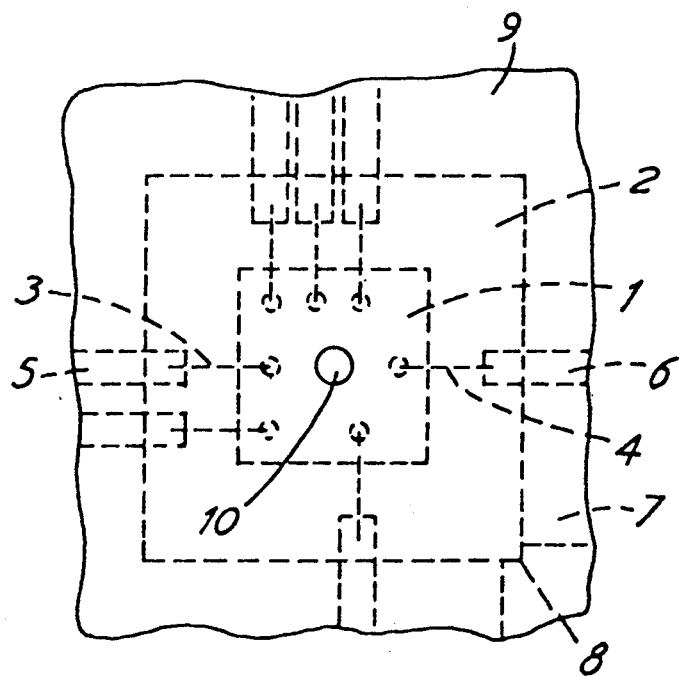
FIG. 3 shows, in plan view, the device of FIG. 2 at the same step in the method.

In FIGS. 2, 3 and 4 the spacers 7 used to prevent the bond wires 3, 4 being excessively depressed are positioned beyond the edges of the chip 1. Alternatively, or additionally spacers 7 may, with advantage be positioned between the chip 1 and the overlying perforated sheet 9. These spacers may either be attached to the chip 1 or be attached to, or from part of, the overlying sheet.

The technique of introducing the encapsulant is common to all methods. A liquid encapsulant (e.g. a uv cross-linkable material) can be placed at the edge of the chip 1 and capillary action pulls the encapsulant over the chip 1 except where the hole 10 opening exists in the sheet 9 over the chemically sensitive region 11. The entire object can then be exposed to uv radiation resulting in cross-linking of the polymer (as shown in FIG. 4). To reduce the possibility of hydrostatic pressure forcing encapsulant over the chip 1 and one the chemically sensitive region 11 through the addition of surplus encapsulant material, the process may be conducted with the substrate 2, and chip 1 and perforated sheet 9, held at an angle such that hydrostatic pressure does not act to cause encapsulant to flood the sensitive area 11. The invention is not predicted on the use of uv-curling encapsulants, and the capillary fill method of introducing and defining the encapsulant may utilise materials cured by visible or other radiation, and indeed may employ encapsulants which are not radiation cured e.g. two part epoxy compositions or silicone rubber sealant preparations. Use of non radiation curing encapsulants does however impose greater constraints on the dimensions of the structures used and the viscosity of the encapsulant.

The use of the invention is compatible with other terms of bonding e.g. tape automatic bonding (TAB) and flip-chip bonding as well as conventional wire bonding. Moreover, the region to be left exposed on the chip 1 (chemically sensitive region) can be precisely defined prior to the application of the encapsulant, by defining the size and shape of the hole 10 in the cover sheet 9, and furthermore, the use of a flow cell cap (as shown in FIG. 6) enables several manufacturing steps to be combined.

Figure 7:
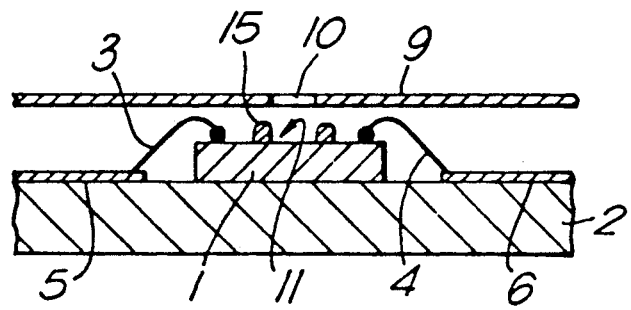

FIG. 7 shows an arrangement where material formed on the chip 1 provides a spacer 15. The material may be in the form of, for example, posts. Such structures are formed from photolithographic techniques on wafers of ISFET devices using suitable thick film photoresist material.

Figure 8:
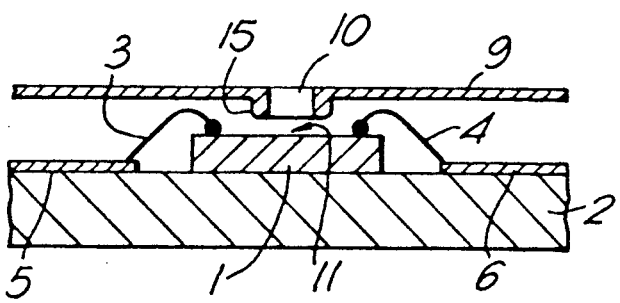
Figure 9:
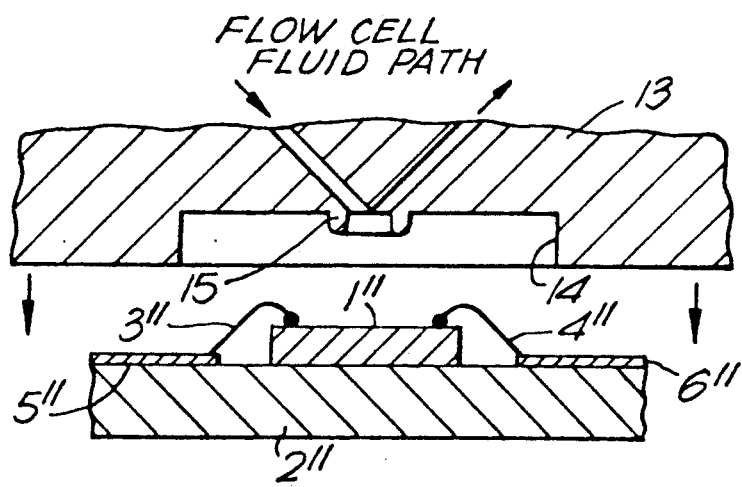

Arrangements where the spacer structure 15 forms part of the perforated sheet or the component overlying the chip are shown in FIGS. 8 and 9 respectively.

Furthermore, it will be appreciated that the spacer structures 7, 14, 15 utilized to prevent the bond wires 3, 4 from being forced into contact with the chip 1 need not only be in the form of posts, but may be isolated ridges, and/or a ridge surrounding the hole 10 which is to be positioned over the chemically sensitive 11 area of the device.

Although photolithographic or screen printing processes may be used to form such spacer structures 7, 14, 15, they may be more conveniently formed by embossing or moulding techniques.

The embossed or moulded structures 7, 14, 15 may be formed in the sheet material before, after or simultaneously with the hole 10 formation; or may be formed as part of the moulding of components such as flow caps.

It will be appreciated by those skilled in the art that the use of sheets or other components bearing spacer structures 7, 14, 15 to overly the ISFET chip 1 requires that before they are brought into contact, the alignment of overlying components and the chip 1 be carried out at a sufficient separation to avoid damage to the band wires 3, 4 by the spacer structures 7, 14, 15.

It will further be appreciated by those skilled in the art that a method in accordance with the present invention is not restricted in its application to that of solely elelctronic devices. The method is equally well applicable to technologies such as optical coupling which may require certain regions to be covered by an encapsulant, but other regions to be free from the encapsulant. Indeed, the invention hereinbefore described is versatile enough to be applicable to technologies of which the inventor is not aware.

We claim:

1. A method for producing a sensor device wherein a liquid encapsulant is applied to a first region of the device but not to a second region of the device, the method comprising;
    (a) defining a passageway along which the encapsulant may be drawn by capillary action, the passageway being bounded in part by the first region of the device and in part by a cover member overlying the device, which cover member is formed with an aperture, substantially registering with the second region, of dimensions sufficient to inhibit capillary action at the second region;
    (b) introducing the encapsulant into the passageway so as to completely cover the first region with the encapsulant whilst leaving the second region free from the encapsulant due to the inhibition of the capillary action.

2. A method according to claim 1 wherein the encapsulant material is allowed or caused to be rendered immobile in relation to the device.

3. A method according to claim 2 wherein the encapsulant material is rendered immobile by exposure to light of a predetermined wavelength.

4. A method according to claim 3 where the light is ultra-violet light.

5. A sensor device produced by enabling a liquid encapsulant to be applied to a first region of the device but not to a second region of the device, the device having a defined passageway along which the encapsulant may be drawn by capillary action, the passageway being bounded in part by the first region of the device and in part by a cover member overlying the device, which cover member is formed with an aperture, substantially registering with the second region, with dimensions sufficient to inhibit capillary action at the second region.

6. A device according to claim 5 wherein the device comprises an ion-selective field effect transistor.

7. A device according to claim 5 further comprising a substrate and an optically transparent cover member; the cover member being held remote from the substrate by support means.

8. A device according to claim 7 wherein the device is an ion-selective field effect transistor device.

9. A device according to claim 7 wherein the support means are formed by photolithography.

* * * * *